United States Patent
Eilers et al.

(10) Patent No.: US 10,227,367 B2
(45) Date of Patent: Mar. 12, 2019

(54) CHLORINATION OF SUCROSE-6-ESTERS

(71) Applicant: Tate & Lyle Technology Limited, London (GB)

(72) Inventors: Thomas Eilers, Cary, IL (US); Halil Aktas, NB Zaandam (NL)

(73) Assignee: Tate & Lyle Technology Limited, London (GB)

( * ) Notice: Subject to any disclaimer, the term of this patent is extended or adjusted under 35 U.S.C. 154(b) by 308 days.

(21) Appl. No.: 15/104,620

(22) PCT Filed: Dec. 15, 2014

(86) PCT No.: PCT/GB2014/053698
§ 371 (c)(1),
(2) Date: Jun. 15, 2016

(87) PCT Pub. No.: WO2015/092374
PCT Pub. Date: Jun. 25, 2015

(65) Prior Publication Data
US 2018/0162892 A1    Jun. 14, 2018

Related U.S. Application Data

(60) Provisional application No. 61/916,419, filed on Dec. 16, 2013.

(51) Int. Cl.
| | |
|---|---|
| C07H 1/06 | (2006.01) |
| C07H 5/02 | (2006.01) |
| C07H 13/04 | (2006.01) |
| C07B 39/00 | (2006.01) |
| C07C 19/08 | (2006.01) |
| C07D 333/48 | (2006.01) |
| C07H 1/00 | (2006.01) |

(52) U.S. Cl.
CPC ............... C07H 1/06 (2013.01); C07B 39/00 (2013.01); C07C 19/08 (2013.01); C07D 333/48 (2013.01); C07H 1/00 (2013.01); C07H 5/02 (2013.01); C07H 13/04 (2013.01)

(58) Field of Classification Search
CPC . C07H 1/06; C07H 5/02; C07H 13/04; C07D 333/48; C07B 39/00; C07C 19/08
USPC ...................................................... 536/122
See application file for complete search history.

(56) References Cited

U.S. PATENT DOCUMENTS

| | | |
|---|---|---|
| 4,380,476 A | 4/1983 | Mufti |
| 4,783,526 A | 11/1988 | O'Brien |
| 4,889,928 A | 12/1989 | Simpson |
| 4,950,746 A | 8/1990 | Navia |
| 5,023,329 A | 6/1991 | Neiditch |
| 5,034,551 A | 7/1991 | Vernon |
| 5,089,608 A | 2/1992 | Walkup |
| 5,298,611 A | 3/1994 | Navia |
| 5,440,026 A | 8/1995 | Khan |
| 5,470,969 A | 11/1995 | Sankey |
| 5,498,709 A | 3/1996 | Navia |
| 5,530,106 A | 6/1996 | Navia |
| 5,977,349 A | 11/1999 | Catani |
| 6,646,121 B2 | 11/2003 | El Kabbani |
| 6,809,198 B2 | 10/2004 | El Kabbani |
| 6,939,962 B2 | 9/2005 | Clark |
| 6,943,248 B2 | 9/2005 | Catani |
| 6,998,480 B2 | 2/2006 | Catani |
| 7,049,435 B2 | 5/2006 | Catani |
| 7,932,380 B2 | 4/2011 | Hao |
| 2006/0188629 A1 | 8/2006 | Liesen |
| 2006/0205936 A1 | 9/2006 | Jia |
| 2006/0276639 A1 | 12/2006 | Fry |
| 2007/0015916 A1 | 1/2007 | Kabbani |
| 2007/0100139 A1 | 5/2007 | Fry |
| 2007/0160732 A1 | 7/2007 | Deshpande |
| 2007/0227897 A1 | 10/2007 | Li |
| 2007/0270583 A1 | 11/2007 | Ratnam |
| 2008/0300401 A1* | 12/2008 | Xu .............................. C07H 1/00 536/127 |
| 2011/0087018 A1 | 4/2011 | Micinski |
| 2012/0077972 A1 | 3/2012 | Boutzale |
| 2012/0095199 A1 | 4/2012 | Hutton |

FOREIGN PATENT DOCUMENTS

| | | |
|---|---|---|
| EP | 0409549 | 1/1991 |
| WO | 2008150379 | 12/2008 |
| WO | 2010109189 | 9/2010 |
| WO | 2010112813 | 10/2010 |
| WO | 2011045565 | 4/2011 |
| WO | 2012071385 | 5/2012 |
| WO | 2012153128 | 11/2012 |
| WO | 2013056128 | 4/2013 |

OTHER PUBLICATIONS

International Search Report and Written Opinion of the International Searching Authority issued in related International Application No. PCT/GB2014/053698 2015.

\* cited by examiner

*Primary Examiner* — Yih-Horng Shiao
(74) *Attorney, Agent, or Firm* — RatnerPrestia

(57) ABSTRACT

There is provided a method for the chlorination of a sucrose-6-acylate to produce a 4,1',6'-trichloro-4,1',6'-trideoxy-galactosucrose-6-acylate, wherein said method comprises the following steps (i) to (v): (i) providing a first component comprising sucrose-6-acylate; (ii) providing a second component comprising a chlorinating agent; (iii) combining said first component and said second component to afford a mixture; (iv) heating said mixture for a heating period in order to provide chlorination of sucrose-6-acylate at the 4, 1' and 6' positions thereof; (v) quenching said mixture to produce a 4,1',6'-trichloro-4,1',6'-trideoxy-galactosucrose-6-acylate; wherein at least one of said first component and said second component comprises a reaction vehicle, and said reaction vehicle comprises a tertiary amide; and wherein said mixture comprises a cosolvent during a least a portion of the heating period of step (iv), wherein said cosolvent comprises perfluorooctane.

18 Claims, No Drawings

CHLORINATION OF SUCROSE-6-ESTERS

CROSS-REFERENCE TO RELATED APPLICATIONS

This is the national phase of International Application No. PCT/GB2014/053698, filed 15 Dec. 2014, which claims priority from U.S. Provisional Application No. 61/916,419, filed 16 Dec. 2013. The disclosure of each of these applications is incorporated herein by reference in its entirety for all purposes.

TECHNICAL FIELD

The present invention relates to an improved method for the production of sucralose. In particular, the present invention relates to a method for the chlorination of a sucrose-6-acylate to afford a sucralose-6-acylate. Sucrose-6-acylate and sucralose-6-acylate are important intermediates in the production of sucralose.

BACKGROUND

Methods for producing sucralose intermediates and sucralose from a feed stream comprising a sucrose-6-acylate in a reaction vehicle are known. For example, EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. The removal of the tertiary amide (which is usually dimethylformamide [DMF]) is carried out by steam stripping. Other methods of extraction of sucralose are known, for example, in U.S. Pat. No. 8,212,022.

Methods for preparing sucrose-6-acylate starting materials for chlorination to sucralose-6-acylate are known, for example, in U.S. Pat. No. 4,950,746; U.S. Pat. No. 4,889,928; U.S. Pat. No. 5,023,329; U.S. Pat. No. 5,089,608; U.S. Pat. No. 5,034,551; U.S. Pat. No. 5,470,969; U.S. Pat. No. 5,440,026; U.S. Pat. No. 6,939,962; and US 2007-0227897.

Other methods of chlorinating sucrose-6-acylate to give sucralose-6-acylate are known, for example, in U.S. Pat. No. 4,380,476; US 2006-0205936; U.S. Pat. No. 7,932,380; and US 2007-0100139.

When a tertiary amide such as DMF is used as a reaction solvent for chlorination, it is known to include a co-solvent in the reaction medium, for example, in US 2011-087018; WO 2011-045565; US 2012-0077972; and US 2012-0095199; as well as in EP 0409549.

Further methods of chlorinating carbohydrates such as sucrose-6-acylates are known in WO 2012/071385 and WO 2013/056128. These two documents disclose a variety of solvents and co-solvents for the chlorination of carbohydrates.

Although methods of making sucralose, and of chlorinating sucrose-6-acylate to give sucralose-6-acylate, are known, there may remain scope to modify the chlorination reaction.

SUMMARY

According to a first aspect of the present invention, there is provided
1) a method for the chlorination of a sucrose-6-acylate to produce a 4,1',6'-trichloro-4,1',6'-trideoxy-galactosucrose-6-acylate, wherein said method comprises the following steps (i) to (v):
(i) providing a first component comprising sucrose-6-acylate;
(ii) providing a second component comprising a chlorinating agent;
(iii) combining said first component and said second component to afford a mixture;
(iv) heating said mixture for a heating period in order to provide chlorination of sucrose-6-acylate at the 4, 1' and 6' positions thereof;
(v) quenching said mixture to produce a 4,1',6'-trichloro-4,1',6'-trideoxy-galactosucrose-6-acylate;
wherein at least one of said first component and said second component comprises a reaction vehicle, and said reaction vehicle comprises a tertiary amide; and
wherein said mixture comprises a cosolvent during a least a portion of the heating period of step (iv), wherein said cosolvent comprises perfluorooctane.

There is further provided:
2) a method according to 1), wherein both of said first component and said second component comprise said reaction vehicle;
3) a method according to 1) or 2), wherein said cosolvent is present in said first component;
4) a method according to 1) or 2), wherein said cosolvent is present in said second component;
5) a method according to 1) or 2), wherein said cosolvent is added to the mixture during step (iii);
6) a method according to 1) or 2), wherein said cosolvent is added to the mixture after step (iii) and before step (iv);
7) a method according to 1) or 2), wherein said cosolvent is added to the mixture during step (iv);
8) a method according to any of 1) to 7), wherein the mixture includes a phase transfer catalyst.
9) a method according to any of 1) to 8), wherein said cosolvent consists of perfluorooctane.
10) a method according to any of 1) to 9) wherein said mixture is heterogeneous during step (iv), having two liquid phases, namely a cosolvent-rich phase and a cosolvent-poor phase.
11) a method according to 10), wherein after step (iv) and before step (v) the cosolvent-rich phase is separated from said mixture.
12) a method according to any of 1) to 8), wherein the cosolvent additionally comprises a further cosolvent, preferably sulfolane.
13) a method according to 12), wherein the cosolvent consists of perfluorooctane and sulfolane.
14) a method according to 12) or 13) wherein said mixture is heterogeneous during step (iv), having two liquid phases, namely a perfluorooctane-rich phase and a sulfolane-rich phase.
15) a method according to 14), wherein after step (iv) and before step (v) the perfluorooctane-rich phase is separated from said mixture.

16) a method according to any of 12) to 15), wherein after step (iv) and before step (v), there is added an antisolvent to thereby produce a solid phase and a liquid phase, wherein the solid phase includes chlorinated carbohydrate product.

17) a method according to claim 16), wherein the solid phase is separated from the liquid phase.

There are further provided methods which further comprise the step of converting at least a portion of said 4,1',6'-trichloro-4,1',6'-trideoxy-galactosucrose-6-acylate to sucralose; and of isolating and purifying the sucralose.

Further features and advantages of the invention will become apparent from the following description of preferred embodiments of the invention, given by way of example only, which is made with reference to the accompanying drawings.

DETAILED DESCRIPTION

A 4,1',6'-trichloro-4,1',6'-trideoxy-galactosucrose-6-acylate can also be referred to as a sucralose-6-acylate, so that 4,1',6'-trichloro-4,1',6'-trideoxy-galactosucrose-6-acetate can also be referred to as sucralose-6-acetate. Both terminologies are used herein.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

As used herein, the term "reaction vehicle" means the diluent or solvent in which the chlorination reaction is performed. The term is meant to indicate that the vehicle may not fully dissolve all the components of the reaction and product mixture. Depending on the chlorinating agent employed, a number of types of reaction vehicles may be used, and any reaction vehicle can be used that is stable under the chlorination conditions and that dissolves the starting materials, reagents, and products at least to some extent. The reaction vehicle according to the present invention comprises a tertiary amide. The tertiary amide reaction vehicle is preferably DMF. The ratio by weight of the tertiary amide reaction vehicle, for example DMF, to total carbohydrate during the chlorination reaction may be from about 1.8:1 to about 13:1, or from about 2.5:1 to about 8:1.

For the avoidance of doubt, in the above "reaction vehicle" is not included any portion that reacts with the chlorinating agent. For example, if the chlorinating agent is Arnold's reagent and the reaction vehicle is DMF, even if the chlorinating agent is added as phosgene which reacts in situ to form Arnold's reagent, those equivalents of DMF are not included in the weight of reaction vehicle for calculating the ratio to carbohydrate.

The first component and/or the second component may be provided in the reaction vehicle.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene) dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis (trichloromethyl) carbonate). Other suitable chlorinating agents known to the skilled person may also be used. Preferably, the chlorinating agent is phosgene or Arnold's reagent.

The chlorinating agent is preferably in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating agent is any amount above three molar equivalents per mole. In a preferred embodiment, the chlorinating agent is provided in an amount of at least seven molar equivalents per mole of the sucrose-6-acylate. Typically, the molar ratio of the chlorinating agent to the sucrose-6-acylate is about 7:1 to about 11:1.

The first component and the second component are combined in step (iii). This is typically conducted at a temperature of from −15 to 55° C., preferably at a temperature of from 0 to 20° C. A typical temperature is 15° C.

When the first component and the second components are combined, the chlorinating agent reacts with the unprotected hydroxyl groups on the sucrose-6-acylate. This is conveniently referred to as "first stage chlorination". For example, when the chlorinating agent is Arnold's reagent, an adduct is formed. The adduct is shown schematically as formula 3 in FIG. 2 of U.S. Pat. No. 4,980,463, which refers to the adduct as "O-alkylformiminium chloride intermediate". This reaction is rapid at around 15° C. Therefore, the time of holding the resulting mixture is not particularly limited. It may be a few minutes, for example from 5 to 30 minutes, or up to several hours, for example from 5 minutes to 24 hours.

The mixture is then heated to achieve chlorination of sucrose-6-acylate at the 4, 1' and 6' positions thereof in step (iv). This is conveniently referred to as "second stage chlorination". In this process, the adduct is converted into the corresponding chloride. At the 4-position of the sucrose adduct, predominant inversion of stereochemistry occurs.

A number of reaction conditions can be used to achieve the chlorination. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, U.S. 2007/0100139, the disclosure of which is incorporated herein by reference, discloses a process in which the reaction mixture is heated between 75° C. to 100° C. to effect chlorination.

In general, the reaction temperature for the chlorination reaction is typically from 85° C. to 130° C. A typical temperature is from 95 to 100° C. It is impractical at atmospheric pressure to exceed 100° C. with DMF as the reaction vehicle and perfluorooctane as the cosolvent, because of the volatility of the mixture.

The reaction time for the chlorination depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products. Typical reaction times are from 1 hour to 24 hours.

In the chlorination reaction, a cosolvent is present, and the cosolvent comprises perfluorooctane. The cosolvent may be present in the first and/or the second component, or it may be added during the combination of the first and second components, or after the two components are combined. The cosolvent is present during at least a portion of the heating period of step (iv). The cosolvent may be present during the whole of the heating period of step (iv).

By "cosolvent" is not meant any particular limitation, other than being a diluent or solvent, in addition to the reaction vehicle, in which the chlorination reaction occurs. It should be compatible with the starting materials, reagents, and reaction products at least to some extent, and should not interfere with the chlorination reaction.

The cosolvent may improve the efficiency and/or the yield of the reaction.

The cosolvent comprises perfluorooctane. The cosolvent may consist essentially of perfluorooctane, or may consist solely of perfluorooctane. Alternatively the cosolvent may additionally comprise one or more further cosolvents. The cosolvent may additionally comprise sulfolane. The cosolvent may consist essentially of perfluorooctane and sulfolane, or may consist of perfluorooctane and sulfolane only. Methods relating to the use of sulfolane as a cosolvent are described in co-pending application PCT/GB2014/052498, which is incorporated herein by reference in its entirety.

The addition of cosolvent sulfolane in particular may reduce the overall degradation of DMF to dimethylamine (DMA), which occurs during second stage of chlorination reaction (See, for example, WO 2010/112813.) It has been found that quenched chlorinated product after chlorination in the presence of cosolvent sulfolane exhibited less DMA than a control experiment without sulfolane. The DMA in the quenched chlorinated product is generally inversely proportional to sulfolane to DMF ratio.

A further cosolvent will typically be an aprotic solvent, and may be an apolar aprotic solvent. A further cosolvent may have a boiling point above 50° C., and may be immiscible with the reaction vehicle and/or with the chlorination mixture.

The ratio by weight of the cosolvent (for example perfluorooctane) to the reaction vehicle (for example DMF) may be from 0.1:1 to 3:1, or from 0.2:1 to 2:1, or from 0.3:1 to 1:1. The ratio is typically approximately 0.5:1.

The ratio of (reaction vehicle+cosolvent) to carbohydrate should preferably be less than 15:1. If reactions are performed more dilute than this then the yield may be adversely affected.

The reaction vehicle and the cosolvent may be selected and presented in an amount such that the chlorination mixture during the heating period in step (iv) is heterogeneous, that is, that it comprises two liquid phases. One phase (which if the reaction vehicle is DMF and the cosolvent is perfluorooctane will usually be the lower phase) will comprise predominantly perfluorooctane, and is referred to herein as the cosolvent-rich phase. The other phase is by definition the cosolvent-poor phase. The reaction vehicle may be immiscible with the cosolvent.

In cases where the cosolvent additionally comprises sulfolane, the reaction vehicle may be miscible with the sulfolane and immiscible with the perfluorooctane components of the cosolvent. In such cases, the phase comprising predominantly perfluorooctane will be referred to herein as the perfluorooctane-rich phase. The other phase is termed the sulfolane-rich phase, and comprises predominantly the sulfolane cosolvent, the reaction vehicle and the chlorinated carbohydrate product (where the product is in solution).

If desired, a phase transfer catalyst may be included in the mixture. The phase transfer catalyst may be included with the cosolvent. Alternatively the phase transfer catalyst may be added separately from the cosolvent, in which case it may be added in the first component, in the second component, or during step (iii), or after step (iii) and before step (iv).

Phase transfer catalysts are known in the art. The phase catalyst may be a quaternary ammonium or phosphonium salt, for example a halide salt thereof such as a chloride salt. A suitable catalyst is Starks' Catalyst (Aliquat 336), which is a quaternary ammonium salt which contains a mixture of $C_8$ (octyl) and $C_{10}$ (decyl) chains with $C_8$ predominating. Starks' Catalyst is known for its catalytic oxidation of cyclohexene to 1,6-hexanedioic acid, as an alternative to traditional oxidation methods of nitric acid or potassium permanganate. Other suitable phase transfer catalysts include, for example, quaternary alkyl, aryl, or mixed alkyl-aryl ammonium halides such as benzyltriethylammonium chloride, benzyltributylammonium chloride, tributyl methylammonium chloride, benzyltrimethylammonium chloride, tetrabutylammonium chloride, methyltrioctylammonium chloride; crown ethers such as 18-crown-6 and dibenzo-18-crown-6; quaternary alkyl, aryl, or mixed alkyl-aryl phosphonium halides such as trihexyltetradecylphosphonium chloride, tetraphenylphosphonium chloride, and hexadecyltributylphosphonium chloride; imidazolium halide salts such as 1-butyl-2,3-dimethylimidazolium chloride, 1-butyl-3-methylimidazolium chloride, 1,2-dimethylimidazolium chloride, and 2-chloro-1,3-dimethylimidazolinium chloride; and pyridinium halide salts such as 1-hexylpyridinium chloride. In the phase transfer catalysts, the alkyl group is generally an alkyl group having from 1 to 10 carbon atoms; the aryl group is generally an aryl group having from 6 to 10 carbon atoms, and is preferably a phenyl group; the imidazolium halide salts are generally substituted on the imidazole portion by from 1 to 3 substituents selected from alkyl group as just defined, aryl group as just defined, and halogen (preferably fluorine, chlorine or bromine) and the halide is preferably chloride; and the pyridinium halide salts are generally substituted on the pyridine portion by from 1 to 2 substituents, including 1 substituent on the 1-position of the pyridine, selected from alkyl group as just defined, aryl group as just defined, and halogen (preferably fluorine, chlorine or bromine) and the halide is preferably chloride.

When a phase transfer catalyst is used, then the mixture may be triphasic for example after combining the chlorinating agent with the sucrose-6-acylate in step (iii), during the heating in step (iv) or both. The mixture may become biphasic, for example during the heating in step (iv), or after the heating in step (iv) but before the quenching in step (v), or both.

Once the chlorination reaction has proceeded to the desired stage of completion, there are a number of procedures that may be employed in order to quench the reaction, remove reaction vehicle and/or cosolvent, and take the material forward to produce sucralose.

In a convenient embodiment of the invention, the cosolvent-rich phase can be separated from the rest of the reaction mixture before chlorination quench, that is, after step (iv) and before step (v). This is a particularly useful manner in which the perfluorooctane cosolvent can be separated and isolated for recovery and reuse.

If desired, a portion of the reaction vehicle (and, if not already removed, cosolvent) may be removed directly from the mixture by distillation before quenching. The resulting distillate is typically made up primarily of the reaction vehicle comprising the tertiary amide along with some acid (typically HCl, in particular when phosgene or Arnold's reagent is used as the chlorinating agent). The removal can be performed according to procedures described in WO 2010/109189, the disclosure of which is incorporated herein by reference in its entirety.

The reaction vehicle (and, if not already removed, cosolvent) may be removed by distillation. This distillation may be conducted under reduced pressure, typically from 1 torr to 200 torr (0.13 to 26.7 kPa), or from 10 torr to 100 torr (1.3 to 13.3 kPa), or from 35 torr to 65 torr (4.7 to 8.7 kPa).

The removal of the reaction vehicle (and, if not already removed, cosolvent) may be carried out at an internal temperature of from 40° C. to 150° C., or from 50° C. to 90° C. The removal of the tertiary amide can be carried out in a batch or continuous manner.

In a batch manner, the removal of the tertiary amide may be carried out over a time period of from 1 hour to 24 hours. The temperature, pressure, and time required are interrelated, and optimum conditions can be determined by the person skilled in the art according to the operating requirements of the process and the equipment used. In general, the removal is carried out as rapidly as possible. If longer time periods are used for the removal, then lower temperatures will generally be used, in order to minimise carbohydrate degradation.

Following chlorination, whether or not any portion of the reaction vehicle and/or cosolvent is removed, the mixture may be quenched, for example with a base, to provide a sucralose-6-acylate and the acid salt of the base.

A number of different bases may be used in the quenching. Bases that can be employed for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most usual base for quenching is sodium hydroxide, due to its ready availability and low cost. Other bases known to the skilled person may also be used for quenching. The quench may be performed with an aqueous solution of the base. The aqueous solution may contain from about 5 wt % to about 50 wt %, typically from about 8 wt % to about 40 wt % of the base. Within these ranges, the solution of the base can be either "concentrated" or "dilute". If the solution of the base is concentrated, then precipitation of salts is envisaged, and in this case suitable concentrations are from 13 to 50 wt %, or from 25 to 45 wt %, or about 35 wt %. If the solution of the base is dilute, precipitation of salts is not envisaged, and in that case suitable concentrations are from 5 to 15 wt %, or from 8 to 13 wt %, or from 10 to 11 wt %.

During the quenching, the pH of the mixture may be controlled, since it may be desired that deacylation should be minimised while quenching takes place. This pH control is readily achievable by controlling the addition rate of the aqueous solution of the base while monitoring the pH within the mixture. Any method of pH-controlled addition known to the skilled person may be used.

Suitably, the pH of the mixture is maintained in the range of from about 7.5 to about 10.5 during the quenching, or from about 8.5 to about 10.5, or from about 9.5 to about 10, or from about 9.5 to about 9.75. The pH may also be maintained at a lower level, for example about 4.5, during the addition, and then raised to the desired pH when all of the base has been added. If deacylation is to be carried out as a separate step, though, a pH of more than about 10 should generally be avoided during quenching, since deacylation may then occur. In order to avoid local extremes of pH, the mixture should be adequately mixed throughout the quenching procedure.

The temperature of the mixture during quenching may suitably be maintained in the range of from above 0° C. to about 80° C., for example, in the range of from 10° C. to 60° C., with a range of from about 12° C. to about 35° C. being typical. The quench may be conducted by the "dual stream quench" method, which is described in U.S. Pat. Nos. 5,530,106 and 5,498,709.

In the dual stream process, the quenching conditions are attained by slow addition of the aqueous base with simultaneous slow addition of feed material into a reaction vessel. The reaction vessel can contain an initial charge of an aqueous solution of the tertiary amide such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction. Generally, the pH should not be permitted to rise above about 10.5 during the course of the quenching reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode. Generally, the pH should not be permitted to rise above about 10.5 during the course of the quenching reaction.

Following quenching, the mixture may be neutralised by the addition of aqueous acid, for example aqueous hydrochloric acid. The sucralose-6-acylate can then be isolated by conventional means, if desired, or deacylation can be carried out without isolation of the sucralose-6-acylate.

After quenching, or in a combined process with the quenching, at least a portion of the 4,1',6'-trichloro-4,1',6'-trideoxy-galactosucrose-6-acylate can be deacylated to afford sucralose. The deacylation can be performed before or after the removal of remaining reaction vehicle and/or cosolvent.

The deacylation can be carried out, for example, by the method disclosed in U.S. Pat. No. 6,890,581, incorporated herein in its entirety by reference. Other methods for deacylating sucralose-6-acylates, and for isolating and/or purifying sucralose, are disclosed in U.S. Pat. No. 5,977,349, U.S. Pat. No. 6,943,248, U.S. Pat. No. 6,998,480, U.S. Pat. No. 7,049,435, U.S. Pat. No. 6,809,198, U.S. Pat. No. 6,646,121, U.S. Pat. No. 5,298,611, U.S. Pat. No. 5,498,709, US2006/0188629, US2006/0276639, US2007/0015916, US2007/0160732, and US2007/0270583, the disclosures of which are all incorporated herein by reference.

The deacylation can be carried out by treatment with a base. Any suitable base may be used, and suitable bases are those already mentioned as the base for quenching. For convenience, the same base may be used for deacylation and quenching. Sodium hydroxide may be used as the base in both cases.

In order to effect deacylation, it is necessary to raise the pH of the mixture, typically to a level above that at which the quenching was carried out. In order to minimise decomposition of the tertiary amide reaction vehicle (if the deacylation is performed before the removal of remaining reaction vehicle and/or cosolvent), the deacylation may be carried out under carefully controlled conditions. Therefore, the deacylation is preferably performed at a pH of from 10 to 13.5, or from 10 to 12, or from 10.5 to 11.2, at a temperature of from 60 to 0° C., or from 40 to 0° C., or from 35° C. to 25° C., the higher pH being used with the lower temperature and vice versa.

If the deacylation is carried out after the removal of remaining reaction vehicle and cosolvent, then the deacylation conditions are less critical, although the above described conditions can still be used. In general, the deacylation may be carried out at a pH of from 8 to 14 and a temperature of from 0 to 60° C., or at a pH of from 10 to 12 and a temperature of from 0 to 40° C.

The deacylation reaction can be conveniently monitored by HPLC. For optimum yields, it is important to monitor the progress of the deacylation reaction, and neutralise the mixture when the reaction is complete. The pH of the mixture should be adjusted to from 6 to 8.5, or approximately 7.5. The mixture can conveniently be neutralised using aqueous hydrochloric acid, or using citric acid or acetic acid. Alternatively, the mixture can be neutralised with gaseous carbon dioxide.

The pH control discussed above in relation to deacylation and subsequent neutralisation is more critical at plant scale; on smaller scales the wider ranges of indicated pH can be employed.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in embodiments described above, it is also possible for quenching and deacylation to be carried out together. In this embodiment, the aqueous solution of a base is added to the chlorination product stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

The removal of remaining reaction vehicle (and, if not already removed, cosolvent) can be carried out by means known in the art, such as distillation, distillation under reduced pressure, steam distillation, steam stripping, or by use of an agitated thin film drier or spray drier.

If the removal of the reaction vehicle (and, if not already removed, cosolvent) is carried out by steam stripping, then such steam stripping can be carried out as described in EP 0708110. Typically, at least 90% of the reaction vehicle present in the mixture at the end of deacylation (if the removal of the reaction vehicle is carried out after deacylation), or after the quench of the chlorination reaction, (if the removal of the reaction vehicle is carried out before the deacylation) is removed during this step. More typically, at least 99% is removed.

If the mixture is concentrated by distillation, then such distillation will typically remove water and reaction vehicle, and may also remove cosolvent, if any is still present. Solids may precipitate as a result of the distillation. The solids may include salts, for example sodium chloride. The solids can be filtered and washed with a suitable solvent, for example methanol or ethanol. The solvent such as methanol or ethanol could be removed, for example by flash distillation. This procedure will generally afford the desired sucralose or sucralose-6-acylate in predominantly DMF and aqueous medium when cosolvent has lower boiling point than water, such as perfluorooctane, and in predominantly DMF and cosolvent when the cosolvent has a higher boiling point than water. The desired product can be isolated by precipitation or by extraction. Extraction can be performed, for example, by using ethyl acetate or methyl tert-butyl ether.

Alternatively or additionally, before or after quenching and/or deacylation, a partitioning solvent may be used to achieve separation of the components of the mixture. For example, addition of a suitable solvent can be used to partition the components. The partitioning solvent can be, for example, ethyl acetate, methyl tert-butyl ether or cyclohexane. The partitioning solvent may be employed in a feed:solvent ratio of from 0.5:1 to 1:3, or from 1:1 to 1:2.

Alternatively or additionally, after quenching and/or deacylation, sucralose can be extracted from an aqueous stream using a suitable solvent, such as ethyl acetate or methyl tert-butyl ether.

In particular cases where the cosolvent additionally comprises sulfolane, an antisolvent may be added to the mixture after step (iv) and before step (v). In this method, the desired carbohydrate product precipitates in the solid phase, while the majority of the reaction vehicle and cosolvent(s) remain in the liquid phase. In one particularly convenient embodiment of the invention, the perfluorooctane-rich phase is firstly separated from the sulfolane-rich phase, thereby removing the perfluorooctane cosolvent. Secondly, the sulfolane-rich phase is treated, before quenching, by addition of an antisolvent which precipitates the chlorinated mass. In this embodiment, the separation of the perfluorooctane-rich phase and the subsequent addition of the antisolvent occurs after step (iv) and before step (v) in the overall reaction scheme.

Preferably, greater than 80% of the chlorinated carbohydrate product is present in the solid phase. In some embodiments greater than 90% or greater than 95% of the chlorinated carbohydrate product is present in the solid phase.

Preferably, greater than 80% of the reaction vehicle is present in the liquid phase. In some embodiments greater than 90% or greater than 95% of the reaction vehicle is present in the liquid phase.

Preferably, greater than 80% of the sulfolane cosolvent is present in the liquid phase. In some embodiments greater than 90% or greater than 95% of the sulfolane cosolvent is present in the liquid phase.

The remaining sulfolane cosolvent and/or reaction vehicle is in the solid phase after addition of the antisolvent.

The antisolvent is any solvent that can preferentially precipitate the chlorinated carbohydrate product. The antisolvent may conveniently be any aprotic solvent that can preferentially precipitate the chlorinated carbohydrate product. The antisolvent can be, for example;
  an acetate ester, such as ethyl acetate, methyl acetate, isopropyl acetate, n-propyl acetate, or n-butyl acetate;
  a ketone, such as acetone, methyl isobutyl ketone, diisobutyl ketone, methyl n-amyl ketone, 2-butanone, 2-pentanone, 3-pentanone, or cyclohexanone;
  an alkyl-substituted benzene, suitably a mono-alkyl substituted or di-alkyl substituted benzene such as toluene, ortho xylene, meta xylene and para xylene or a mixture of xylenes;
or mixtures thereof. Particularly convenient antisolvents are ethyl acetate, acetone and toluene, more particularly ethyl acetate and acetone.

After addition of the antisolvent, the solid phase can be separated from the liquid phase, for example by filtration, or by decantation. The remaining reaction vehicle and/or sulfolane cosolvent in the solid phase can be removed by washing the solid phase with antisolvent, and/or by redissolving solid phase first in a suitable dry solvent, such as reaction vehicle, and then addition of antisolvent to precipitate the chlorinated carbohydrate product for a second time. This multiple washing and/or redissolving step with subsequent precipitation process of the solid phase increases sulfolane cosolvent removal efficiency.

The liquid phase will comprise reaction vehicle, sulfolane cosolvent and antisolvent (as herein defined) which can be collected, separated, and recycled for further use. Suitable methods for separating the reaction vehicle, sulfolane cosolvent and antisolvent include distillation.

The solid phase will comprise the chlorinated mass including the desired chlorinated carbohydrate, possibly with residual reaction vehicle, sulfolane cosolvent and/or antisolvent (as herein defined). This can then be quenched as described herein. This step is according to step (v) of the claimed reaction sequence. After quenching, the product can be deacylated to afford sucralose, if desired.

EXAMPLES

Arnold's Reagent, chlorodimethylformiminium chloride, CAS 3724-43-4 (purity of 98.4% with the remaining assumed to be DMF), and Aliquat 336 (Starks' catalyst) were purchased from Alfa Aesar. Perfluorooctane was purchased from Sigma Aldrich and dried over activated 4 Å molecular sieves.

A stock solution of sucrose-6-acetate has the following composition.

| Description | % of total, w/w |
| --- | --- |
| Sucrose-6-acetate | 33.06 |
| Other carbohydrates | 6.58 |
| DMAc (Dimethyl acetamide) | 0.35 |
| Acetic acid | 1.15 |
| Water | 0.08 |
| DMF (Dimethyl formamide) | Remaining |

Control Experiment without Co-Solvent
Ratio DMF:Carbohydrate=8.6:1

A jacketed 500 mL multi-neck reaction flask, equipped with overhead stirrer, thermometer, addition funnel, inert gas (nitrogen) inlet, and condenser was charged with 26.70 g of commercial Arnold's Reagent (purity of 98.4%) and with 64.50 g of DMF. The obtained off-white to yellow coloured slurry was cooled to 15° C. and then 23.07 g of a sucrose-6-acetate (33.06% wt.) stock solution in DMF (from stock solution described above) was added to the slurry over a period of 15-30 min after which the reaction mass was heated to room temperature and kept at 20° C. for 12 h resulting in a homogeneous orange to light brown reaction mixture. Then the reaction mixture was heated to an internal temperature of 96° C. over a period of 45 min and held at this temperature for 19 h. After completion of the chlorination reaction, and cooling of the mixture down to room temperature, dual stream quench and simultaneous deacylation steps were performed by using 110 g DMF:water (ratio 1:3) heel and 114.81 g 12% NaOH (aq.) at pH 11.6, at 30° C., and held for 2 h. Then the quenched mixture was neutralized to pH 9.5 with HCl (37% wt.) and after 1 hour a sample was assayed by HPLC to give 62.30% molar sucralose yield from combining 4,1',6'-trichlorogalactosucrose-6-acylate (sucralose-6-acetate), 4,1',6'-trichloro-4,1',6'-trideoxygalactosucrose (sucralose), and 3',6'-anhydro-4,1'-dichloro-4,1'-dideoxy-galacto-sucralose.

Repeated chlorination of sucrose-6-acetate in DMF as chlorination vehicle, under identical conditions and reaction scale, gave average molar yield of 62%.

Example 1—Chlorination with Perfluorooctane Cosolvent

Ratio DMF:Carbohydrate=5.9:1 and DMF:Perfluorooctane=1:0.5

A jacketed 500 mL multi-neck reaction flask, equipped with overhead stirrer, thermometer, addition funnel, inert gas (nitrogen) inlet, and condenser was charged with 28.59 g of commercial Arnold's Reagent (purity of 98.4%) and with 42.60 g of DMF. The obtained off-white to yellow coloured slurry was cooled to 15° C. and then 24.60 g of a sucrose-6-acetate (33.06% wt.) stock solution in DMF (from stock solution described above) was added to the slurry over a period of 15-30 min after which the reaction mass was heated to room temperature and kept at 20° C. for 12 h. To the resulting homogeneous orange to light brown reaction mass 26.30 g perfluorooctane was added. DMF to co-solvent ratio was approximately ~1:0.5. At this stage the perfluorooctane and chlorination mass were separate phases. The reaction mixture was heated to an internal temperature of 96° C. over a period of 45 min and held at this temperature for 19 h. At this stage the perfluorooctane and chlorination mixture were mixing to some extent, but were separate phases and both perfluorooctane and chlorination mixture were refluxing so that perfluorooctane was efficiently mixing with the chlorination mixture. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 20.0 g, with 76% recovery without work-up). The top phase, which was dark coloured chlorination mixture, was dual stream quenched and simultaneously deacylated using 110 g DMF:water (ratio 1:3) heel and 129.50 g 12% NaOH (aq.) at pH 11.6, at 30° C., and held for 2 h. Then the quenched mixture was neutralized to pH 9.5 with HCl (37% wt.). After 1 hour a sample was assayed by HPLC to give 65.46% sucralose yield from combining sucralose-6-acetate, sucralose, and 3',6'-anhydro-4,1'-dichloro-4,1'-dideoxy-galacto-sucralose.

In this experiment, the addition of perfluorooctane gave an increase of sucralose yield of over 3% compared with the control experiment.

Example 2—Chlorination with Perfluorooctane Cosolvent

Ratio DMF:Carbohydrate=5.7:1 and DMF:Perfluorooctane=1:0.5

Similar to Example 1, to a slurry of 25.72 g of commercial Arnold's Reagent (purity of 98.4%) in 36.70 g DMF was added 22.31 g sucrose-6-acetate (33.06% wt.) stock solution in DMF (from stock solution described above) to react at 15° C. Then, after 12 hours 26.2 g perfluorooctane was added. DMF to co-solvent ratio was approximately ~1:0.5. 110 g DMF:water (ratio 1:3) heel and 118.45 g 12% NaOH (aq.) were used to quench giving 66.85% sucralose yield from combining sucralose-6-acetate, sucralose, and 3',6'-anhydro-4,1'-dichloro-4,1'-dideoxy-galacto-sucralose.

In this experiment, the addition of perfluorooctane gave an increase of sucralose yield of over 4% compared with the control experiment.

Example 3—Chlorination with Perfluorooctane Cosolvent—Addition of Perfluorooctane to Chlorinating Agent Before Addition of Substrate Ratio DMF:Carbohydrate=4.5:1 and DMF:Perfluorooctane=1:1.2

A jacketed 500 mL multi-neck reaction flask, equipped with overhead stirrer, thermometer, addition funnel, inert gas (nitrogen) inlet, and condenser was charged with 27.90 g of commercial Arnold's Reagent (purity of 98.4%) and with 28.00 g of DMF and 50.00 g of perfluorooctane. The obtained off-white to yellow coloured slurry was cooled to 15° C. Perfluorooctane separates from DMF and Arnold's Reagent as a clear layer as the bottom phase. Then 24.10 g of a sucrose-6-acetate (33.06% wt.) stock solution in DMF (from stock solution described above) was added to the slurry over a period of 15-30 min after which the reaction mass was heated to room temperature and kept at 20° C. for 12 h. DMF to co-solvent ratio was approximately ~1:1.2. At this stage the perfluorooctane and chlorination mass were separate phases. The reaction mixture was heated to an internal temperature of 96° C. over a period of 45 min and held at this temperature for 19 h. At this stage the perfluorooctane and chlorination mixture were mixing to some extent, but were separate phases and both perfluorooctane and chlorination mixture were refluxing so that perfluorooctane was efficiently mixing with the chlorination mixture. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 44.9 g, with 90% recovery without work-up). The top phase, which was dark coloured chlorination mixture, was dual stream quenched and simultaneously deacylated using 110 g DMF:water (ratio 1:3) heel and 125.48 g 12% NaOH (aq.) at pH 11.6, at 30° C., and held for 2 h. Then the quenched mixture was neutralized to pH 9.5 with HCl (37% wt.). After 1 hour a sample was assayed by HPLC to give 65.74% sucralose yield from combining sucralose-6-acetate, sucralose, and 3',6'-anhydro-4,1'-dichloro-4,1'-dideoxy-galacto-sucralose. Recovered perfluorooctane was assayed for impurities and solvents giving 288 ppm DMF, 9 ppm acetate, 2 ppm DMA, 3 ppm sodium without chloride. The impurities in the recovered perfluorooctane are low, thus perfluorooctane can be reused in chlorination reaction without further clean-up.

In this experiment, the addition of perfluorooctane gave an increase of sucralose yield of over 3% compared with the control experiment.

Example 4—Chlorination with Perfluorooctane Cosolvent—Addition of Phase Transfer Catalyst Ratio DMF:Carbohydrate=3.7:1 and DMF:Perfluorooctane=1:1

A jacketed 500 mL multi-neck reaction flask, equipped with overhead stirrer, thermometer, addition funnel, inert gas (nitrogen) inlet, and condenser was charged with 28.00 g of commercial Arnold's Reagent (purity of 98.4%), 21.00 g of DMF, 35.00 g of perfluorooctane and 0.15 g Aliquat 336. Aliquat 336 (Starks' catalyst) is a quaternary ammonium salt used as a phase transfer catalyst. It contains a mixture of $C_8$ (octyl) and $C_{10}$ (decyl) chains with $C_8$ predominating. After the slurry was cooled down to 15° C. and then 24.21 g of a sucrose-6-acetate (33.06% wt.) stock solution in DMF (from stock solution described above) was added over a period of 15-30 min, the mixture resulted in three phases. This indicates that Aliquat 336 helps to mix the co-solvent and chlorination mixture forming a third intermediate phase. Upon heating the reaction mixture first to room temperature and keeping at 20° C. for 12 h, the reaction mixture was further heated to an internal temperature of 96° C. over a period of 45 min and held at this temperature for 19 h. DMF to co-solvent ratio was approximately ~1:1. At this stage (and especially as the temperature rose to above 70° C.) the reaction mixture became two separate phases and the mixture was refluxing. After completion of the chlorination reaction and cooling of the mixture down to room temperature, the perfluorooctane and the chlorination mixture were two separate phases. Perfluorooctane, a clear heavy phase, was discharged from the drain of the reactor in an amount of 28.84 g (82% recovery). The top dark-colored chlorination mixture was dual stream quenched and simultaneously deacylated using 20 g DMF:water (ratio 1:3) heel and 133.84 g 12% NaOH (aq.) at pH 11.6, at 30° C., and held for 2 h. Then the quenched mixture was neutralized to pH 9.5 with HCl (37% wt.) and after 1 hour a sample was assayed by HPLC to give 65.43% sucralose from combining sucralose-6-acetate, sucralose, and 3',6'-anhydro-4,1'-dichloro-4,1'-dideoxy-galacto-sucralose. Recovered perfluorooctane was assayed for impurities and solvents giving 0.22% DMF, 100 ppm acetate, 7 ppm acetate, 100 ppm sodium, 4 ppm chloride but no DMA was detected. The impurities in the recovered perfluorooctane are low, thus perfluorooctane can be reused in chlorination reaction without further clean-up.

In the second control example and example 5 (both below) the reagents used were as follows; Arnold's Reagent, chlorodimethylformiminium chloride, CAS 3724-43-4, perfluorooctane, and sulfolane, which were purchased from Sigma Aldrich.

Another stock solution of sucrose-6-acetate has the following composition and was used in the second control example and example 5 below.

| Description | % of total, w/w |
| --- | --- |
| Sucrose-6-acetate | 38.00 |
| Other carbohydrates | 5.77 |
| DMAc (Dimethyl acetamide) | 0.31 |
| Water | 0.08 |
| Acetic acid | 0.65 |
| DMF (Dimethyl formamide) | Remaining |

A typical composition of the DMF is as follows:

| Description | % of total, w/w |
| --- | --- |
| Water | 0.16 |
| DMF (Dimethyl formamide) | Remaining |

Control Experiment 2 without Co-Solvent

Ratio DMF:Carbohydrate=12:1

A jacketed 500 ml multi-neck reaction flask, equipped with overhead stirrer, thermometer, addition funnel, inert gas (nitrogen) inlet, and condenser was charged with 25.40 g of commercial Arnold's Reagent (purity of 95.0%) and with 91.80 g of DMF. The obtained off-white to yellow coloured slurry was cooled to 0-5° C. and then 19.85 g of a sucrose-6-acetate (38.00% wt.) stock solution in DMF (from stock solution described above) was added to the slurry over a period of 15-30 min after which the reaction mass was heated to room temperature and kept at 25° C. for 2 h resulting in homogeneous orange to light brown reaction mixture. Then the mixture was heated to an internal temperature of 100° C. over a period of 45 min and held at this temperature for 11 h. After completion of the chlorination reaction, and cooling of the mixture down to room temperature, dual stream quench was performed using 11% NaOH at pH 9.9. Then the quenched mixture was neutralized to pH 8.5 with HCl (33% wt.).

Samples were assayed by HPLC to give 60.23% molar sucralose yield from combining sucralose-6-acetate and sucralose, and by ion chromatography (IC) to give 16252 ppm DMA.

Example 5—Chlorination with Perfluorooctane and Sulfolane Co-Solvent Combination Ratio DMF:Carbohydrate=4:1, DMF:Sulfolane=1:1, and DMF:Perfluorooctane=1:1

A jacketed 500 mL multi-neck reaction flask, equipped with overhead stirrer, thermometer, addition funnel, inert gas (nitrogen) inlet, and condenser was charged with 25.07 g of commercial Arnold's Reagent (purity of 95.0%) and with 21.99 g of DMF and with 34.30 sulfolane. The obtained off-white to yellow colored slurry was cooled to 0-5° C. and then 19.59 g of a sucrose-6-acetate (38.00% wt.) stock solution in DMF (from stock solution described above) was added to the slurry over a period of 15-30 min. after which the reaction mass was heated to room temperature and kept at 25° C. for 2 h. Then 34.30 g perfluorooctane was added to the resulting homogeneous orange to light brown reaction mass and then the reaction mixture was heated to 100° C. over a period of 45 min. DMF to sulfolane ratio was approximately ~1:1 and DMF to perfluorooctane ratio was approximately ~1:1. The internal temperature was held at this temperature for 11 h. After completion of the chlorination reaction and cooling of the mixture down to room temperature, the perfluorooctane and the chlorination mixture were two separate phases. Perfluorooctane, a clear heavy phase separating at the bottom of the reactor, was discharged from the drain of the reactor, and was collected separately (weight of perfluorooctane was 29.87 g, with 87.1% recovery without work-up). The top phase, which was dark colored chlorination mixture, was dual stream quenched using 11% NaOH at pH 9.9 and 15° C. Then the quenched mixture was neutralized to pH 8.5 with HCl (33% wt.).

Samples were assayed by HPLC to give 68.61% molar sucralose yield from combining sucralose-6-acetate and sucralose, and by IC to give 5379 ppm DMA.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method for the chlorination of a sucrose-6-acylate to produce a 4,1',6'-trichloro-4,1',6'-trideoxy-galactosucrose-6-acylate, wherein said method comprises the following steps (i) to (v):
    (i) providing a first component comprising sucrose-6-acylate;
    (ii) providing a second component comprising a chlorinating agent;
    (iii) combining said first component and said second component to afford a mixture;
    (iv) heating said mixture for a heating period in order to provide chlorination of sucrose-6-acylate at the 4, 1' and 6' positions thereof;
    (v) quenching said mixture to produce a 4,1',6'-trichloro-4,1',6'-trideoxy-galactosucrose-6-acylate;
    wherein at least one of said first component and said second component comprises a reaction vehicle, and said reaction vehicle comprises a tertiary amide; and
    wherein said mixture comprises a cosolvent during a portion of the heating period of step (iv), wherein said cosolvent consists of perfluorooctane or perfluorooctane and sulfolane.

2. The method according to claim 1, wherein both of said first component and said second component comprise said reaction vehicle.

3. The method according to claim 1, wherein said cosolvent is present in said first component.

4. The method according to claim 1, wherein said cosolvent is present in said second component.

5. The method according to claim 1, wherein said cosolvent is added to the mixture during step (iii).

6. The method according to claim 1, wherein said cosolvent is added to the mixture after step (iii) and before step (iv).

7. The method according to claim 1, wherein said cosolvent is added to the mixture during step (iv).

8. The method according to claim 1, wherein the mixture further includes a phase transfer catalyst.

9. The method according to claim 1, wherein said cosolvent consists of perfluorooctane.

10. The method according to claim 1 wherein said mixture is heterogeneous during step (iv), having two liquid phases, namely a cosolvent-rich phase and a cosolvent-poor phase.

11. The method according to claim 10, wherein after step (iv) and before step (v) the cosolvent-rich phase is separated from said mixture.

12. The method according to claim 1, wherein the cosolvent consists of perfluorooctane and sulfolane.

13. The method according to claim 12, wherein said mixture is heterogeneous during step (iv), having two liquid phases, namely a perfluorooctane-rich phase and a sulfolane-rich phase.

14. The method according to claim 13, wherein after step (iv) and before step (v) the perfluorooctane-rich phase is separated from said mixture.

15. The method according to claim 1, wherein after step (iv) and before step (v), the method further comprises a step of adding an antisolvent to thereby produce a solid phase and a liquid phase, wherein the solid phase includes chlorinated carbohydrate product.

16. The method according to claim 15, wherein the solid phase is separated from the liquid phase.

17. The method according to claim 1, wherein the method further comprises the step of converting at least a portion of said 4,1',6'-trichloro-4,1',6'-trideoxy-galactosucrose-6-acylate to sucralose.

18. The method according to claim 17, wherein the method further comprises the step of isolating and purifying the sucralose.

\* \* \* \* \*